United States Patent [19]

Friedman

[11] 4,369,791
[45] Jan. 25, 1983

[54] BODY IMPLANTABLE ELECTRODE
[75] Inventor: Harry G. Friedman, Plymouth, Minn.
[73] Assignee: Medtronic, Inc., Minneapolis, Minn.
[21] Appl. No.: 253,865
[22] Filed: Apr. 13, 1981

Related U.S. Application Data

[63] Continuation of Ser. No. 80,539, Oct. 1, 1979, abandoned.

[51] Int. Cl.³ ............................................... A61N 1/04
[52] U.S. Cl. ................................................ 128/419 P
[58] Field of Search ....... 128/419 P, 419 PG, 419 PS, 128/783, 784

[56] References Cited

U.S. PATENT DOCUMENTS

| | | | |
|---|---|---|---|
| 3,543,761 | 12/1970 | Bradley | 128/419 E |
| 3,735,766 | 5/1973 | Bowers et al. | 128/419 P |
| 3,835,864 | 9/1974 | Rasor et al. | 128/419 PG |
| 4,157,720 | 6/1979 | Greatbatch | 128/419 P |

*Primary Examiner*—William E. Kamm
*Attorney, Agent, or Firm*—Schroeder, Siegfried, Vidas, Steffey & Arrett

[57] ABSTRACT

A body implantable electrical stimulator including stimulation impulse developing circuitry and an output system, including active and indifferent electrodes, for delivering the impulses to stimulate a desired body site. The indifferent electrode is formed as an annular member having a regular electrode-forming surface. The annular member may be electrically closed or open, the distal end being insulated in the latter case. In a preferred embodiment, the impulse developing circuitry is housed in an encapsulant and the annular member is partially imbedded in the encapsulant at the periphery of the housing. Two or more annular members may be employed in a multi-channel device to provide isolation between channels.

10 Claims, 6 Drawing Figures

BODY IMPLANTABLE ELECTRODE

This is a continuation of application Ser. No. 6/080,539, filed Oct. 1, 1979 and now abandoned.

BACKGROUND OF PRIOR ART

Monopolar lead systems are known in the field of electrical body stimulation. Typically, such systems employ a single lead having an active electrode near the distal end thereof with an indifferent electrode, often in the form of a relatively large, flat, metal plate, located on the exterior of the housing for the circuitry which develops the stimulation signal. In such a system, the electrical impulses occur between the active electrode at the distal end of the lead and the plate. The plate is sufficiently large such that the current density does not result in stimulation of the adjacent tissue.

It has been found that with an indifferent plate electrode the bulk of the charge transfer is at the periphery with little or no charge transfer at the central region. It is essentially the surface area of the periphery of the plate that establishes current density and determines whether local stimulation will occur. Thus, the formation of an indifferent electrode as a plate requires an unnecessary amount of electrode material to result in unnecessary expense, particularly if a noble metal is employed. In addition, the use of a plate requires a bonding of that plate to the surface of the housing which has, in the past, caused problems.

One approach to the elimination of the indifferent plate electrode is disclosed in U.S. Pat. No. 3,788,329, issued Jan. 29, 1974, for BODY IMPLANTABLE LEAD, in the name of Harry G. Friedman, which is co-owned with the present invention. In the referenced patent, an indifferent lead section is provided in the form of a conductor wrapped, as coils, around a portion of the length of the lead body. The coils are spaced from each other so as to increase the effective surface area. However, this type of arrangement requires two connectors, one for each of the active and indifferent electrodes. Thus, while the referenced patent does eliminate the plate indifferent electrode, it nonetheless imposes size constraints on the entire unit in that two connector assemblies must be employed.

BRIEF SUMMARY OF THE INVENTION

The present invention provides an indifferent electrode of sufficient surface area to reduce current density and prevent stimulation at the indifferent electrode site while also eliminating the prior art plate configuration and the necessity for a connector assembly for the indifferent electrode. An annular member is provided with a regular electrode-forming surface and may be formed as an open or closed ring. In a preferred embodiment, stimulation impulses are developed by suitable circuitry which are housed in an encapsulant with the annular member being carried at the periphery of the housing. The annular member may be partially imbedded in the encapsulating material and, if the member is electrically open, the distal end thereof may be electrically insulated, preferably by the encapsulating material itself. In multi-channel devices, multiple annular members may be provided to form isolated indifferent electrodes for channel isolation.

DETAILED DESCRIPTION OF INVENTION

Figure 1:
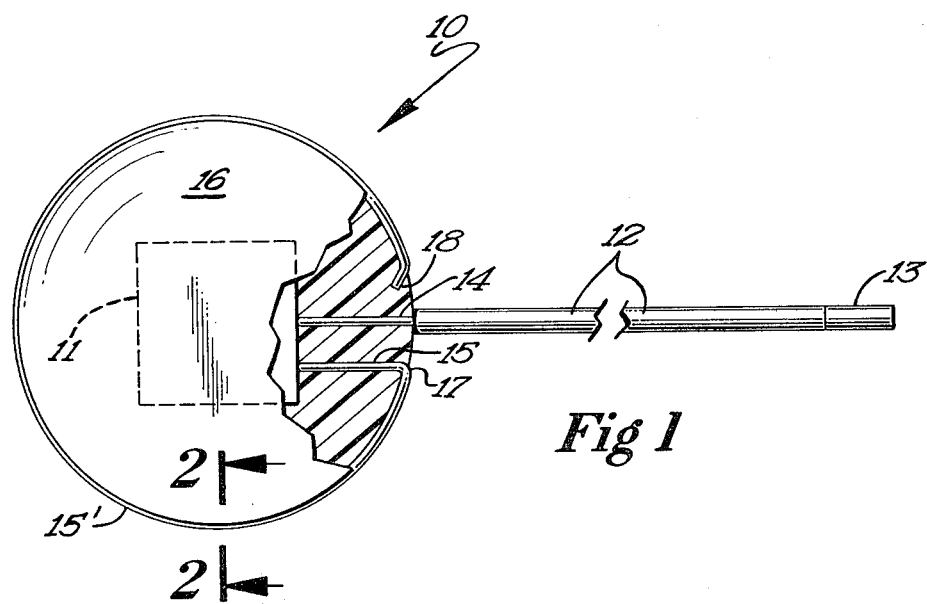
FIG. 1 is an illustration of a preferred embodiment of the present invention.

Referring now to FIG. 1, there is illustrated a body implantable electrical stimulator generally designated at 10 including stimulation impulse developing circuitry 11 and a lead 12 which terminates at an active electrode 13. The stimulation impulse developing circuitry 11 may be a pulse generator of a type known to the prior art or, alternatively, may be a radio frequency receiver, also of a type known to the prior art. In either case, the impulse developing circuitry 11 is connected to the active electrode 13 via a conductor 14, in known manner. Another conductor 15 is also connected to the impulse developing circuitry 11 with that circuitry and portions of the conductors 14 and 15 being contained within a housing 16 which may be formed of a biocompatible encapsulating material, in known manner. The lead 12 may be directly connected to the impulse developing circuitry 11 or, alternatively, may be interconnected therewith via a connector assembly, in known manner.

As illustrated in FIG. 1, the conductor 15 emerges from the housing 16 at the point 17 to be wrapped around the periphery of the housing 16 to form an electrically open ring with distal end 18 being imbedded within the housing 16. The material forming the housing 16 is an electrically insulating material thereby providing insulation to the distal end 18 of the conductor 15. The end 18 of conductor 15 need not be imbedded within the housing 16 but is preferably insulated for reasons which will become apparent from the following discussion.

The exposed surface of conductor 15 provides an electrode forming surface to function as an indifferent electrode of sufficient surface area to avoid stimulation of adjacent body tissue while eliminating the need for an indifferent electrode plate. However, any sharp turns within the exposed portion of conductor 15 or any non-uniform surface irregularities will result in an increase in the current density at their location. Thus, the exposed portion of conductor 15 should be free of sharp turns and non-uniform surface irregularities. That is, the electrode-forming surface should be regular. For this reason, distal end 18 of conductor 15 should also be insulated, as by imbedding it within the housing 16, or otherwise.

Figure 2:
FIG. 2 is a cross-section taken along the line 2—2 of FIG. 1 illustrating a preferred indifferent electrode configuration.
Figure 3:
FIG. 3 is a cross-section taken along the line 2—2 of FIG. 1 illustrating another preferred indifferent electrode configuration.
Figure 4:
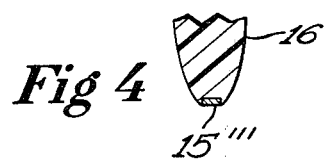
FIG. 4 is a cross-section taken along the line 2—2 of FIG. 1 illustrating yet another preferred indifferent electrode configuration.

Referring now to FIG. 2, which is a cross-section taken along the line 2—2 of FIG. 1, there is illustrated a preferred embodiment for the conductor 15. Specifically, the conductor 15', having a generally circular cross-section, is partially imbedded within the housing 16. The exposed surface of the conductor 15' is the electrode-forming surface. Another embodiment of an electrode-forming conductor is illustrated in FIG. 3 where a conductor 15" is illustrated partially imbedded within the housing 16. The conductor has an irregular surface. However, the surface irregularities are imbedded within the housing 16 such that the exposed surface of conductor 15" is regular. FIG. 4 illustrates an additional electrode-forming conductor in the form of a band 15''' having a generally rectangular cross-section with three surfaces of the band 15''' being insulated by the material forming the housing 16 as by being imbedded therein. The exposed surface of conductor 15'''' presents a regular electrode-forming surface.

Figure 5:
FIG. 5 is a cross-section taken along the line 2—2 of FIG. 1 illustrating still another preferred indifferent electrode configuration.
Figure 6:
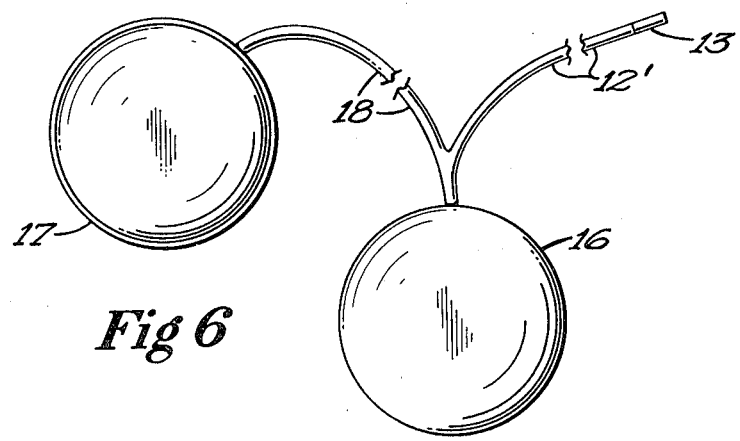
FIG. 6 illustrates another preferred embodiment of the present invention.

Obviously, many modifications and variations of the present invention are possible in light of the above teachings. For example, if the circuitry 11 is pulse-generating circuitry, the conductor 15 may be a complete or electrically closed ring. In addition, the conductor need not be carried at the outermost periphery of the housing 16 but may be carried anywhere at its surface. In addition, two or more conductors may be employed as in a multi-channeled device to provide channel isolation. An example of multiple conductors being carried by the housing 16 at a location other than its outermost periphery is illustrated in FIG. 5. It should be noted that positioning the conductor at the outermost periphery provides a greater length of conductor and therefore a greater exposed surface area for a given housing size. However, surface area can be otherwise increased as by employing a conductor of a larger size or as by uniformly sandblasting the exposed surface of the conductor to increase the exposed surface while avoiding non-uniform surface irregularities. Further, the electrode-forming structure of the present invention need not be carried by the housing 16 but, instead, may be positioned remotely from the housing 16 to communicate with the circuitry contained within the housing 16 via a lead in known manner. An annular electrode-forming member is illustrated in FIG. 6 as ring 17 which is electrically interconnected with the circuitry within housing 16 via a lead 18, in known manner. Lead 18 may be separate from the lead for the active electrode 13 or may merge with that lead such as that illustrated at 12' in FIG. 6, in known manner. It is therefore to be understood that, within the scope of the appended claims, the invention may be practiced otherwise than as specifically described.

I claim:

1. A body implantable stimulator which comprises:
   stimulation impulse developing means;
   generally disc-shaped means of an electrically insulating material housing said impulse developing means;
   impulse delivering means incuding active electrode means carried by a lead extending from said housing; and,
   annular indifferent electrode means carried at the periphery of said housing means, said indifferent electrode means being partially imbedded in said insulating material and having an exposed electrode-forming surface that is regular and large in relation to said active electrode.

2. The stimulator of claim 1 wherein said annular indifferent electrode means comprises electrically open ring means and further comprising means electrically insulating the distal end of said ring means.

3. The stimulator of claim 2 wherein said distal end insulating means comprises a portion of said encapsulating means.

4. The stimulator of claim 1 wherein said annular means comprises electrically closed ring means.

5. The stimulator of claim 1 wherein said stimulation impulse developing means comprises receiver means, said annular indifferent electrode means comprising electrically open ring means.

6. The stimulator of claim 1 wherein said stimulation impulse developing means comprises pulse generator means.

7. The stimulator of claim 1 wherein said annular indifferent electrode means comprises electrically open ring means and further comprising means electrically insulating the distal end of said ring means.

8. The stimulator of claim 1 wherein only a portion of the surface of said annular indifferent electrode means is exposed, said exposed indifferent electrode surface being regular.

9. The stimulator of claim 8 wherein said annular indifferent electrode means comprises multiple, electrically isolated annular means.

10. The stimulator of claim 1 wherein said annular indifferent electrode means comprises multiple, electrically isolated annular means.

* * * * *